(12) United States Patent
Tacke et al.

(10) Patent No.: US 6,316,646 B1
(45) Date of Patent: *Nov. 13, 2001

(54) PROCESS FOR THE CONTINUOUS CATALYTIC TRANSFORMATION OF ORGANIC COMPOUNDS

(75) Inventors: Thomas Tacke, Friedrichsdorf; Stefan Röder, Sinntal; Inge Beul, Gründau; Steffen Laporte, Rodgau; Peter Panster, Rodenbach, all of (DE)

(73) Assignee: Degussa AG, Hanau (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/073,810

(22) Filed: May 7, 1998

(30) Foreign Application Priority Data

May 12, 1997 (DE) ............................................... 197 19 431

(51) Int. Cl.[7] ........................... C07C 51/36; C07C 31/18; C07C 5/00
(52) U.S. Cl. .......................... 554/144; 554/145; 554/147; 568/861; 585/264
(58) Field of Search .................................. 554/144, 145, 554/147; 568/861; 585/264

(56) References Cited

U.S. PATENT DOCUMENTS

| 3,969,382 | 7/1976 | Zosel . |
| 4,278,609 | * 7/1981 | Kuiper . |
| 4,714,591 | * 12/1987 | Avedesian . |
| 5,626,756 | 5/1997 | Heidlas et al. ........................ 210/634 |

FOREIGN PATENT DOCUMENTS

| 0 721 980 A2 | 7/1996 | (EP) . |
| 44 47 116 | 7/1996 | (DE) . |
| WO95 22591 | 8/1995 | (WO) . |
| WO95/22591 | 8/1995 | (WO) . |
| WO96 01304 | 1/1996 | (WO) . |

OTHER PUBLICATIONS

Tacke et al.: "Hardening of Fats and Oils in Supercritical CO2", *Process Technology Proceedings*, NL, Elsevier, Amsterdam.

* cited by examiner

Primary Examiner—James O. Wilson
Assistant Examiner—Leigh C. Maier
(74) Attorney, Agent, or Firm—Smith, Gambrell & Russell LLP (57) ABSTRACT

A process for the continuous catalytic conversion of organic compounds, that, together with unwanted attendant materials, form a starting substance: first the organic compounds of the starting material are purposely extracted by means of condensed fluids. Then the extract, containing the condensed fluids and organic compounds as the reaction mixture is contacted with a catalyst for the catalytic conversion of the organic compounds to form a product mixture, which contains the individual products of the catalytic conversion. The product mixture is separated from the reaction mixture and the fluids employed are, optionally, conducted back for extraction.

16 Claims, 5 Drawing Sheets

PROCESS FOR THE CONTINUOUS CATALYTIC TRANSFORMATION OF ORGANIC COMPOUNDS

INTRODUCTION AND BACKGROUND

The present invention relates to a process for the catalytic transformation of one or more organic compounds that, together with unwanted attendant materials, form a starting substance.

In chemistry the necessity frequently exists to carry out a catalytic transformation or conversion of a mixture of organic compounds that, along with the desired starting substance, contains undesired attendant or impurity substances, which either interfere with the catalytic reaction or are unwanted and undesired in the final product. Among the catalytic reactions that are under consideration in this context are included, for example, alkylation, acylation, esterification, transesterification, oxidation, or hydrogenation reaction, all of which are well known and understood in the art. The starting substances to carry out these reactions can be natural or synthetic.

A commercially very important example of such a reaction is the catalytic hydrogenation of fats, oils, fatty acid esters and free fatty acids from natural sources, which are also referred to herein as fatty raw materials. The objective of the hydrogenation of these organic compounds is to hydrogenate partially or completely the double bonds, without affecting other functional groups of the compounds, for example the carboxyl group, in the process. The complete hydrogenation of these compounds is characterized as hardening, since their melting points are increased by this. If it is intended that only a certain number of the double bonds be hydrogenated, then it is referred to as selective hydrogenation. The hydrogenation occurs catalytically with the assistance of hydrogen.

Fats and oils from natural sources contain attendant and impurity substances, which are undesired in their later application and also act as catalysts poisons and lead to a faster deactivation of the hydrogenation catalysts. Within the context of this invention, all substances that decrease the catalytic activity—regardless of their chemical nature or their source—are characterized as catalyst poisons. It therefore involves the naturally occurring materials in fats and oils, as well as decomposition products or materials that are, however, introduced during the processing and reactions (H. Klimmek, JAOCS, Vol. 61, No. 2, Feb. 1984). This category of undesired components includes in particular sulfur, phosphorous, chlorine and nitrogen compounds, as well as, for instance oxidized fatty acids, soaps and water.

Before the hydrogenation takes place of the fats, oils, fatty acid ester and free fatty acids, the starting substances are therefore liberated from the undesired attendant materials in a separate step. This can take place with fats and oils through a chemical or physical refinement process and with free fatty acids that usually are refined through vacuum distillation. According to the degree of purity of the starting materials, the purification process can be carried out in stages. In vacuum distillation for the purification of free fatty acids, decomposition products can indeed result, since the fatty raw materials are easily thermally decomposable. The decomposition products frequently cause an unpleasant odor of the distilled products, which must be remedied by deodorization. The deodorization is carried out only after the hydrogenation. Because of the thermal sensitivity of the products, with a short contact time, a low temperature in the processing is to be maintained as much as possible.

Since about 1970, condensed gases have been used for the extraction, refinement, deodorization and fractionation of fatty raw materials, as for example in DE 23 63 418 C3, U.S. Pat. No. 4,156,688, DE 35 42 932 A1, DE 42 33 911, DE 43 26 399 C2, EP 0 721 980 A2 and DE 44 47 116 A1. These processes describe the use of condensed gases in the sub-critical (liquefied), near critical and supercritical condition, whereby compared to the distillation procedures, the processes using condensed gases are conducted under relatively favorable processing conditions.

Today, cooking oils and free fatty acids are hardened to the extent of over 99%, either batch wise in a stirred tank, or in tubular reactors. In these process, powder form nickel-diatomite or nickel-silica catalysts are used for hydrogenation, which catalysts must be removed through filtration after the hydrogenation. Disadvantageously, in such processes, there are low space-time yields and the formation of undesirable side products as a consequence of the limited transport of hydrogen to the catalyst by diffusion from the gas phase through the liquid phase. Moreover, these processes have high costs, for example, for personnel, energy and filtration. The filtration decreases the product yield, since hardened product remains in the filter residue.

The nickel-diatomite or nickel-silica catalyst forms a considerable portion of so-called trans-fatty acids in the hardening of cooking oil. This fact is of particular disadvantage, since trans-fatty acids are suspected of increasing the fatty content and cholesterol content in human blood.

With the hardening of free fatty acids for oleo-chemical applications, the nickel-diatomite or nickel-silica catalyst deactivates through the formation of so-called nickel soaps. These remain in the product and must be separated by distillation. Nickel soaps represent a waste product and must be removed at considerable cost.

For the avoidance of the previously mentioned disadvantages of the batch hardening, or the use of nickel-diatomite or nickel-silica catalysts, continuous processes were developed in which palladium fixed bed catalysts come into use. The patents, or patent applications that describe the state of the art on this are CA 1 157 844, DE 41 09 502 C2 and DE 42 09 832 A1 or EP 0 632 747 B1.

According to DE 41 09 502 C2, the continuous hardening of crude fatty acids in the trickle bed is carried out with a palladium/titanium oxide catalyst. The reaction media are therefore added in the form of a 2-phase mixture of liquid fatty acids and hydrogen gas with the fixed bed catalyst for the reaction. The hydrogenation activity in this process thereby permits a space velocity of only $1.2\ h^{-1}$. The catalyst in this process has a limited resistance to the catalyst poisons contained in the crude fatty materials. Also here, a separate purification of the starting substances cannot, however, be foregone in the industrial application of the catalyst for the reduction of the catalyst consumption.

WO 95/22591 and WO 96/01304 describe processes in which super-critical fluids are used as solvents for fats, oils, free fatty acids, free fatty acid esters and hydrogen. According to WO 95/22591, the cited compounds with the hydrogen necessary for the hydrogenation and in the presence of a supercritical fluid are thereby transformed with a catalyst, and then separated by it through release of the supercritical fluid. The supercritical fluids make possible in this process an improved material transport, in particular for hydrogen, and an improved heat exchange. Moreover, the viscosities of the reaction medium are lowered, so that clearly increased space time yields and improved selectivity can be obtained.

No statements are made for the necessary purity of the starting substance for this process.

Through the purification stages added as a rule to the hydrogenation process, one manages to clearly lower the consumption of catalyst per ton of hardened fatty acids in the batch hardening with nickel-diatomite or nickel-silica catalyst, as well as in the continual hardening in the presence of supercritical fluids.

U.S. Pat. No. 3,969,382 describes the simultaneous hydrogenation and deodorizing of fats and oils in the presence of supercritical carbon dioxide, hydrogen and a finely divided nickel-hydrogenating catalyst at temperatures of 100 to 250° C. and a pressure of 150 to 300 bar. The catalyst, after the hydrogenation, is separated out from the hardened products through a filter press. The simultaneous hydrogenation and deodorization has the disadvantage, that the catalyst comes directly into contact with the catalyst poisons and is deactivated.

The state of the art for the hydrogenation of fatty raw materials thus describes batch or continuous processes, which, nevertheless, are only in a limited way insensitive to the catalyst poisons contained in the starting substance, and which, as a rule, require the purification of the starting substance in a separate stage of purification. Similar relationships occur with the other processes carried out as pure treatments.

An object of the present invention is therefore to provide a process for the catalytic transformation or conversion of organic compounds, which makes possible the purification of the starting substance and the catalytic transformation of the organic compounds in a single process.

SUMMARY OF THE INVENTION

The above and other objects of the present invention are achieved by a continuous process for the catalytic conversion of a starting material comprising one or more organic compounds together with one or more undesirable attendant or impurity materials. In carrying out the invention, first the desired organic compounds contained in the starting substance are purposefully extracted by means of condensed fluids. The extract formed b condensed fluids and organic compounds is conducted as a reaction mixture, possibly with the addition of further reactants, in contact with a catalyst, whereby there occurs the catalytic transformation of the organic compounds to a product mixture, which contains the individual products of the catalytic transformation. The product mixture is separated from the reaction mixture and the fluids used are withdrawn and optimally recycled for extraction.

As used herein, the term "condensed fluids" excludes hydrogen, and is intended to include fluids, which, under the chosen extraction and reaction conditions (temperature and pressure), have either a vapor pressure which is less than the chosen pressure, and thus are present in the liquid state, or which are found under the chosen reaction conditions in the near critical, critical or supercritical state. By the term "near critical" is meant conditions under which the chosen temperature Tk (T<Tk) and the chosen pressure p are greater than or equal to the critical pressure pk ($p \geq pk$) with respect to the particular fluid.

Extraction and catalytic transformation are predominantly carried out at temperatures ranging from 0 to 300° C. and pressures ranging from 10 to 800 bar.

The condensed fluids serve in the process according to the invention as solvents for the organic compounds in the raw material and for the further reactants. Such fluids are therefore chosen which have a good dissolving capability for these substances under the extraction and reaction conditions of the process. In this regard, butane, ethane, carbon dioxide, propane, dinitrogen monoxide or mixtures thereof have shown themselves to be especially suitable fluids.

The extraction is preferably carried out working in countercurrent flow with the cited fluids. It can be performed in typical extractors. In this way, the organic compounds are dissolved in the condensed fluids and are drawn off as extract through the head of the extractor, while the undesirable attendant materials including organic compounds, especially with hetero-atoms (P, S, N), and inorganic compounds which dissolve poorly, are collected at the bottom of the extractor as waste. Here they are drawn off periodically.

To increase of the purity of the organic compounds, the extraction can be carried out in multiple stages. A further improvement of the extraction is obtained through addition of so-called modifiers to the condensed fluids. The term "modifiers" means materials that increase the solubility of the organic compounds in the condensed fluids. Suitable modifiers are polar organic compounds such as acetone and/or $C_1$–$C_6$-alcohols.

The extract consists of the condensed fluids and the organic compounds dissolved therein. According to the catalytic reaction carried out, the extract is conducted in contact with a suitable catalyst, or only after addition of a further reactant such as oxygen for oxidation reactions or hydrogen for hydrogenations. Depending on the specific case, additional condensed fluids can also be mixed in at this stage. The organic compounds contained in the reaction mixture are transformed with the catalyst. According to the make up of the organic compounds in the raw material starting substance (for example, free fatty acids with various chain lengths), a product including from various individual products is obtained by the catalytic conversion.

In the carrying out of hydrogenation reactions, hydrogen can be used in a multiple stoichiometric excess, in order to provide the catalytically active sites of the catalyst with sufficient hydrogen. Since the dissolving capability of the fluids, as a rule, is not sufficient for the reception of the entire quantity of hydrogen, either additional supercritical fluids are added along with the hydrogen, in order to make possible the complete solubility of the hydrogen in the fluid, or the excess hydrogen is conducted as pressurized gas, together with the reaction mixture, in contact with the catalyst.

The separation of the product mixture from the reaction mixture can be carried out in a simple way through reduction of the pressure or through increase of the temperature. The pressure is, for example, decreased, so that the fluids pass into the gas phase and the product mixture stays behind. Alternatively, the solubility of the product mixture in the reaction mixture can be decreased through increase in the temperature, so that likewise a separation of the product mixture from the reaction mixture results. With the separation of the product mixture, it can just as well also be broken down into its individual products through correspondingly fractionated pressure reduction, or temperature increase.

BRIEF DESCRIPTION OF DRAWINGS

The present invention will be further understood with reference to the accompanying drawings, wherein.

DETAILED DESCRIPTION OF INVENTION

A preferred area of implementation of the process according to the invention is the selective or complete hydrogenation of fats, oils, fatty acid esters and free fatty acids. In contrast to U.S. Pat. No. 3,969,382, the situs of the purification of the starting substance in the process according to the invention is separated by extraction from the situs of the hydrogenation. In the process according to the invention, an extractor connected in-line and a hydrogenation reactor are used. First, the starting substance is purified. It is then transformed in the purified state in the hydrogenation reactor. In this way, clearly improved catalyst retention times can be achieved. If, by contrast, hydrogenation and deodorization of fats and oils are simultaneously carried out, as in U.S. Pat. No. 3,969,382, then the catalyst comes into contact with catalysts poisons. The consequences of the prior known process are reduced retention times of the catalysts used.

For the hydrogenation of fats, oils, fatty acid esters and free fatty acids, all known hydrogenation catalysts can be used, such as nickel, platinum, rhodium, or ruthenium catalysts, or combinations thereof on silicic acid or silicium dioxide, aluminum oxide, titanium oxide, zircon oxide, magnesium oxide, active charcoals or mixed oxides such as magnesium aluminate. The platinum metal groups on formed carriers have proven themselves especially well. The catalytic activity can be influenced by promoters. Thus it is known, for example, that silver, as a promoter for nickel and palladium catalysts, reduces the formation of trans-isomers.

The carriers should have a high specific surface area, in order to make possible a good dispersion of the catalyst metals. Specific surface areas of between 10 and 1000 $m_2/g$ measured according to BET are beneficial. The pore structure of the carriers is also important. They should have a total pore volume of between 0.05 and 6.5 ml/g, which consists primarily of mesopores and macropores. Micropores are undesirable and should make up only a slight percentage of the total pore volume.

The concepts of micro-, meso-, and macro-pores are used here in conformity with the appropriate definitions of IUPAC incorporated herein by reference. According to these definitions, the pore groups include the following diameter ranges:

micro pores: d<2 nm meso pores: d=2 . . . 50 nm macro pores: d>50 nm

Meso and micro pores, through their large pore diameters, guarantee an optimal accessibility of the catalytically active precious metal crystals deposited on their surface area for the fat, fatty acid or fatty acid ester molecules. This accessibility is supported by the fact that the condensed fluids used have a low viscosity.

The content of platinum group metals on the carrier should amount to between 0.05 and 5% by weight, preferably between 0.1 and 3.0% by weight.

The platinum group metals must be deposited on the carrier in finely divided distribution, in order to make available as large a metal surface area as possible for the catalytic process. A measure for the size of the catalytically active metal surface area is the adsorption of carbon monoxide. Depending on the content of platinum group metals, it should lie between 0.05 and 5.0 ml CO/g of the prepared catalyst bodies.

The catalyst carriers can be formed as desired according to known technology. Appropriate for this are, in particular, all forms known for fixed bed catalysts, thus spheres, cylinders, hollow cylinders and open spoke wheels as well as monolithic catalyst beds in the form of honeycomb bodies with parallel flow channels or foam ceramics with open pore systems. The monolithic honeycomb bodies can generally consist of carrier material with high surface area (complete catalyst) or be constructed of an inert support body with a coating made out of the high surface area carrier material (coating catalyst).

Through the low viscosity of the condensed fluids it is possible to use relatively small particle size catalyst carriers as a particle catalyst, without the pressure drop over the catalyst bed being too large. Catalysts with outer dimensions in the range between 0.1 and 5.0 mm, in particular between 0.2 and 3.0 mm are advantageous. In this way, very high activity levels can be achieved. Spherical form carriers are preferable.

Because of the small dimensions of the catalysts, they have in the bulk filling a very high geometric surface area relative to the total volume of the bulk filling. This is of benefit to the catalytic activity of the catalyst bulk filling. This activity can be improved further, if the platinum group metals are deposited on these carriers in an external shell of 10–40 $\mu$m in thickness. The shell impregnation is of special significance for the selective fat hardening. It specifically hinders fat molecules, which are diffused into the interior of the catalyst carrier, from staying in contact with catalytically active metals for a long time and thereby fully hardening. For the complete hardening of fats or fatty acids, by contrast, fully impregnated catalyst carriers can also be used.

Various materials are suitable as catalyst carriers. They must indeed fulfill the above cited requirements for their physical characteristics, and be resistant to the reaction media, in particular to the fatty acids. With the conventional fat hardening, active charcoals, silicon dioxide, aluminum oxide, aluminum/silicon mixture oxide, barium sulfate, titanium oxide, with titanium oxide coated glass beads and ion exchange resins have been well proven. These carrier materials can also be used in the process according to the invention. The cited requirements are satisfied in an optimal way, however, by organo-siloxanamine copolycondensates, by polymers, secondary and/or tertiary organosiloxanamine compounds, or by organosiloxane-polycondensates. These carrier materials are described in the German patent documents DE 38 00 563 C1, DE 38 00 564 C1, DE 39 25 359 C1, DE 39 25 360 C1 and DE 42 25 978 C1. The patent documents DE 41 10 705 C1 and DE 41 10 706 C1 make known catalysts on the basis of platinum group metals.

Figure 1:
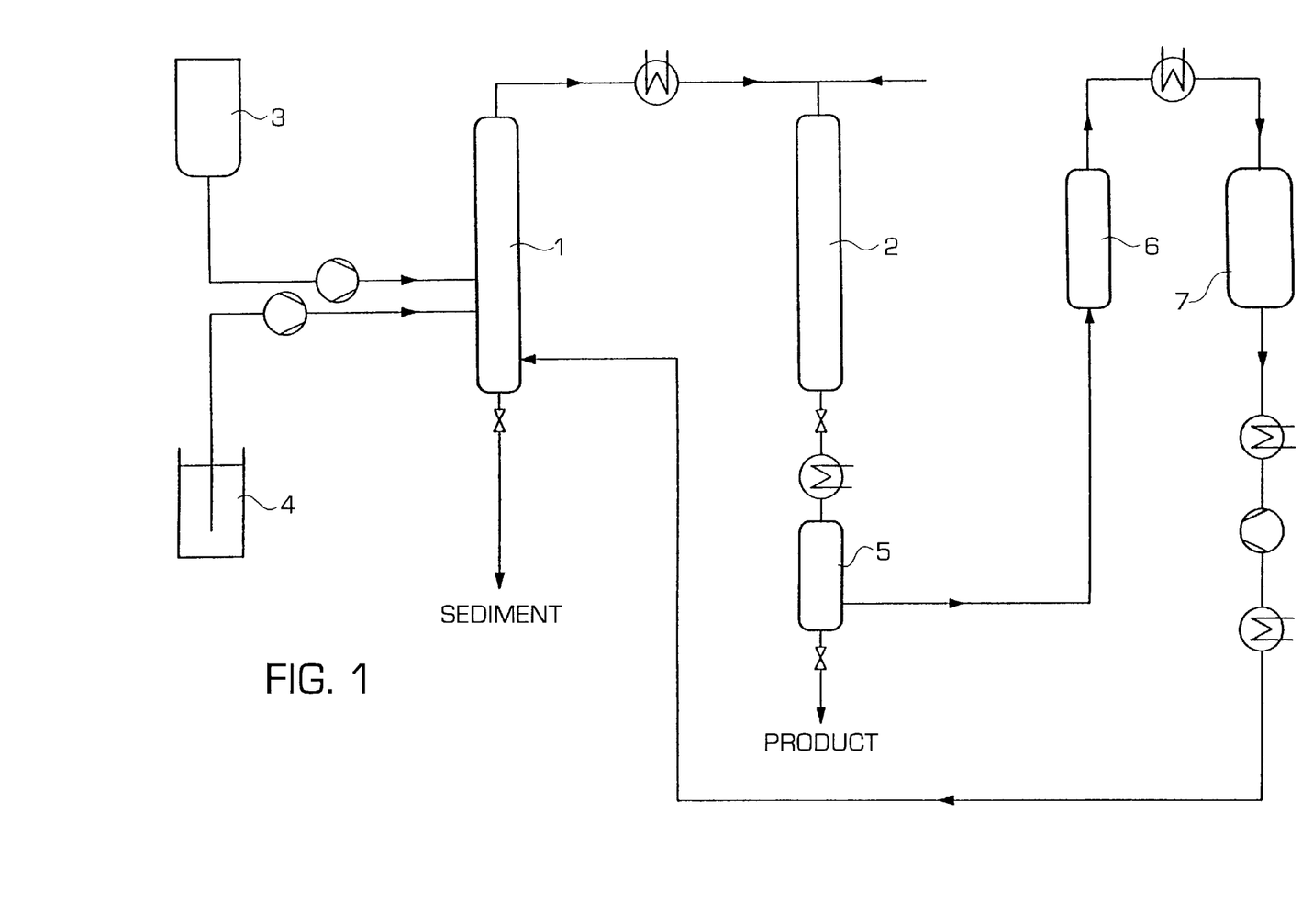
FIG. 1 is a schematic flow diagram of the overall process according to the invention.

The following examples serve for the further explanation of the invention. FIG. 1 shows the schematic representation of the test apparatus used for the examples. The extraction column 1 can typically be a 1000 mm long special steel pipe with an inner diameter of 30 mm, filled with so-called CY "Sulzer packs" made out of metal mesh. The column is operated in the counter current flow process. The condensed fluids serve as the extraction medium and are supplied to the column from below and distributed to a height of 120 mm through a disk. The resulting sediment can collect in the space remaining below (extraction well) and be evacuated intermittently. The extract flow is removed at the head of the extractor. The starting substance which is the raw fat material, for example, is found in the storage tank 3 and is supplied to the extraction column 1 at a level of 420 mm, so that the extraction apparatus is subdivided into a 300 mm long "extraction part" (pure extraction) and a 580 mm long "concentration part" (enrichment of the extract). A modifier stored in the storage tank 4 can be employed to influence the dissolving capability of the extraction medium. The modifier is supplied either separate from or together with the starting substance or extraction medium into the extraction column.

The extraction column is electrically heated with several heating units, so that various temperature gradients can be employed along the extractor. In particular, the extractor head, an area of about 100 mm in length, can be heated more intensely than the remaining extraction column. In this way, the solubility of the extracted material in the extraction medium is reduced and an internal extract reverse movement in the column is implemented. Similar to a rectification, the purity of the extract can thus further be increased.

The extract arrives from above into the hydrogenation reactor 2, which is typically formed of a 750 mm long special steel pipe with an inner diameter of 15 mm. This special steel pipe is filled in the bottom third with a catalyst volume of 5 ml. Stuffing material, such as a web made of quartz fiber wool is found above and beneath the catalyst mixture. They separate the basic catalyst bed of glass beads, which fill up the remaining open volume of the special steel pipe above and beneath the catalyst mixture. The inert mixture above the catalyst mixture serves simultaneously as a static mixer for the mixing of the various media and reactants. The reactor 2 is electrically heated. The hydrogen required for the hydrogenation is added together with the extract to the reactor from above. Extract and hydrogen form the reaction mixture.

After running down through the reactor 2, the reaction mixture arrives in a separator 5. In the separator, the reaction mixture is broken up into the fluid product mixture, gaseous fluid and residual hydrogen by pressure reduction to beneath the critical pressure. The separated fluid and the residual hydrogen can either be released into the atmosphere or, after being re-liquefied or condensed, be carried back for extraction. For this purpose, the gas mixture is cleaned in an adsorber 6 and stored in the buffer tank 7.

All lines of the test apparatus and the storage tank for the fatty acids used are electrically heated.

With the test apparatus of FIG. 1, pretests were first conducted with various fluids for countercurrent flow extraction of crude fatty acids. The extract and the extraction waste were thus examined at predetermined time intervals for iodine number, acid number and sulfur content.

The iodine number is a measure for the quantity of double bonds not yet hydrogenated in the product and is stated in grams of iodine absorbed by 100 g of the sample. It is determined according to the official Tg1-64 (Wijs-method) method of the A.O.C.S.

The acid number is used for the determination of the content of free organic acids in the oil (see German Dispensatory 7th edition, 1968). It specifies how many mg KOH are necessary to neutralize the free acids contained in 1 g fat or oil. The acid number is a measure of the purity of the extracted fatty acids. The lower the acid number, the more foreign materials are contained in the fatty acid.

The sulfur content was detected through a Wickbold-decomposition of the fatty acids and subsequent ion chromatography. The sulfur content serves as a measurement number for possible catalyst poisons contained in the fatty acid, for example: sulfur, phosphorous, nitrogen and chlorine compounds.

The crude fatty acid used essentially consisted of oleic acid and had the following statistical characteristics:

| iodine number: | 56 g iodine/100 g crude fatty acid |
| --- | --- |
| acid number: | 187.9 mg KOH/g crude fatty acid |
| sulfur content: | 84 mg/kg |

Five extraction trials A through E were conducted with varying fluid mixtures and extraction conditions. The chosen extraction conditions are listed in Table 1. Table 2 records the extraction results.

The critical state measures of the carbon dioxide and propane used in these trials are given by:

| $CO_2$: | Tk = 31° C.; | Pk = 73 bar |
| --- | --- | --- |
| propane: | Tk = 96° C.; | Pk = 42 bar |

As detailed in Table 1, the crude fatty acid can be purified with $CO_2$, $CO_2$/propane, $CO_2$/acetone mixtures at 200 bar, and with subcritical propane and propane/$CO_2$ mixtures at 35 bar.

With $CO_2$ and $CO_2$/acetone mixtures, very high purities were attained. The low sulfur contents and the clearly improved acid numbers explain this also. However, comparatively low yields are attained. With propane/$CO_2$ mixtures, the yields could be substantially improved at 200 bar as well as at 35 bar operating pressure with good purity. With liquid propane at 35 bar, the highest yields could be achieved.

TABLE 1

| | | | Extraction parameters: | | | | |
| --- | --- | --- | --- | --- | --- | --- | --- |
| Trial | Pressure [Bar] | Crude Fatty Acid (Mass Flow) [g/h] | CO2 (Volume Flow) [Nl/h] | Propane (Volume Flow) [Nl/h] | Acetone (Volume Flow) [Nl/h] | Temperature (Extractor) [° C.] | Temperature (Extractor Head) [° C.] |
| A | 200 | 6–7 | 150 | — | — | 60 | 61 |
| B | 200 | 6–7 | 150 | — | 6 | 73 | 90 |
| C | 200 | 6–7 | 135 | 25 | — | 83 | 100 |
| D | 35 | 6–7 | — | 100 | — | 52 | 60 |
| E | 35 | 6–7 | 25 | 100 | — | 52 | 60 |

TABLE 2

Results for the extraction:

| Trial | Yield [Extract] [% By Weight] | Sulfur Content [Extract] [mg/kg] | Acid Number [Extract] [mg KOH/g] | Sulfur Content Extraction Waste [mg/kg] | Acid Number Extraction Waste [mg KOH/g] |
|---|---|---|---|---|---|
| A | 45.4 | 22 | 198.35 | 102 | 179.3 |
| B | 59.4 | 22 | 197.3 | 102 | 180.5 |
| C | 95.2 | 19 | 193.1 | 535 | 133.8 |
| D | 99.0 | not determined | not determined | 1050 | not determined |
| E | 94.7 | not determined | not determined | 210 | not determined |

EXAMPLE 1

The hydrogenation of crude fatty acid, as per the process according to the invention, with integrated purification of the crude fatty acid by extraction with a $CO_2$/propane mixture was carried out under the following processing conditions

| | |
|---|---|
| Volume flow $CO_2$: | 135 N/h |
| Volume flow propane: | 25 N/h |
| Volume flow $H_2$: | 1–100 N/h |
| Temperature in the extractor | 80° C. |
| Temperature at the extractor head | 100° C. |
| Reaction temperature: | 140–190° C. |
| Pressure: | 200 bar |
| LHSV: | 1 h$^{-1}$ |

For the hydrogenation, a 1% Pd/OFP catalyst was used. Pd/OFP stands for a palladium catalyst on a carrier made of an organo-functional polysilaxane as per example 2 of the patent document DE 44 05 029 C2 which is relied on and incorporated herein for that purpose. In this patent document, the hydrogenation characteristics of this catalyst in supercritical media and its physical-chemical characteristic numbers are described.

The above specified space velocity (LHSV =Liquid Hourly Space Velocity) is related to the employed catalyst volume of 5 ml.

Figure 2:
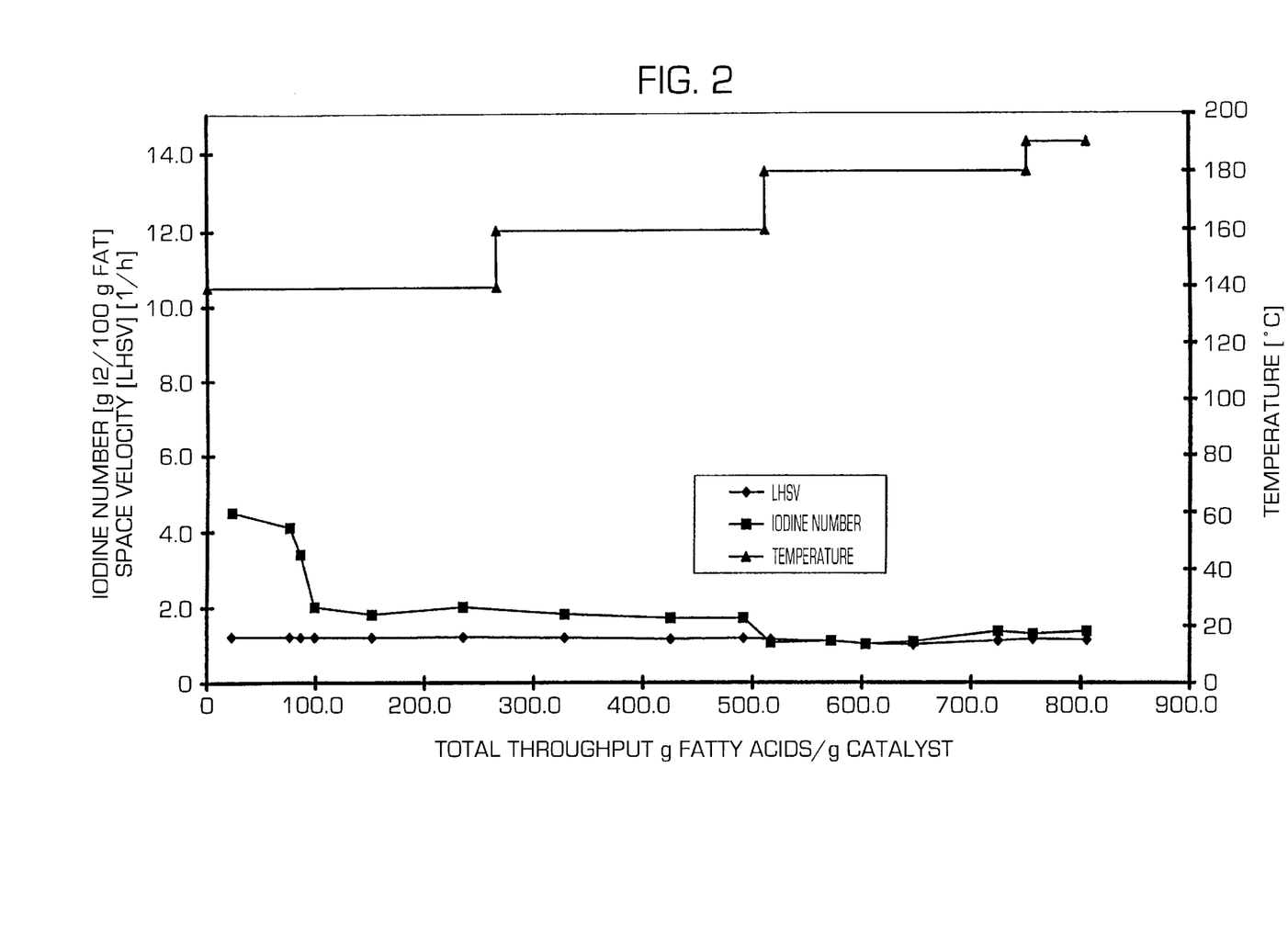
FIG. 2 is a plot of iodine number, temperature and space velocity related to the hardening of fatty acids in combination with in-situ extraction at 200 bar.

Table 3 and FIG. 2 describe the course of the procedure. An iodine number of 1–2 was achieved up to a flow total through out of 800 g of fatty acid per g of catalyst. Through increase in temperature after a specific conversion of about 235 g of fatty acid per gram of catalyst, a possible deactivation of the catalyst was prevented, and a further reduction of the iodine number was achieved.

TABLE 3

| Time | T [° C.] | LHSV [h$^{-1}$] | Iodine Number $\left[\frac{g\ I_2}{100\ g}\right]$ | Total Throughput $\left[\frac{g\ Fatty\ Acid}{g\ Catalyst}\right]$ |
|---|---|---|---|---|
| 8.33 | 140.00 | 1.21 | 4.50 | 22.29 |
| 22.75 | 140.00 | 1.20 | 4.10 | 75.91 |
| 26.08 | 140.00 | 1.19 | 3.40 | 85.85 |
| 30.08 | 140.00 | 1.19 | 2.00 | 99.31 |
| 46.42 | 140.00 | 1.19 | 1.80 | 152.10 |
| 71.25 | 140.00 | 1.20 | 2.00 | 235.47 |
| 98.42 | 160.00 | 1.18 | 1.80 | 328.57 |

TABLE 3-continued

| Time | T [° C.] | LHSV [h$^{-1}$] | Iodine Number $\left[\frac{g\ I_2}{100\ g}\right]$ | Total Throughput $\left[\frac{g\ Fatty\ Acid}{g\ Catalyst}\right]$ |
|---|---|---|---|---|
| 124.58 | 160.00 | 1.15 | 1.70 | 424.98 |
| 142.83 | 160.00 | 1.17 | 1.70 | 491.86 |
| 149.75 | 160.00 | 1.13 | 1.04 | 516.91 |
| 166.58 | 160.00 | 1.09 | 1.10 | 572.26 |
| 176.38 | 160.00 | 1.02 | 1.01 | 603.38 |
| 190.50 | 160.00 | 1.00 | 1.08 | 646.72 |
| 214.67 | 160.00 | 1.10 | 1.35 | 724.57 |
| 223.72 | 190.00 | 1.14 | 1.28 | 756.04 |
| 238.75 | 190.00 | 1.12 | 1.35 | 805.45 |

COMPARISON EXAMPLE 1

Figure 3:
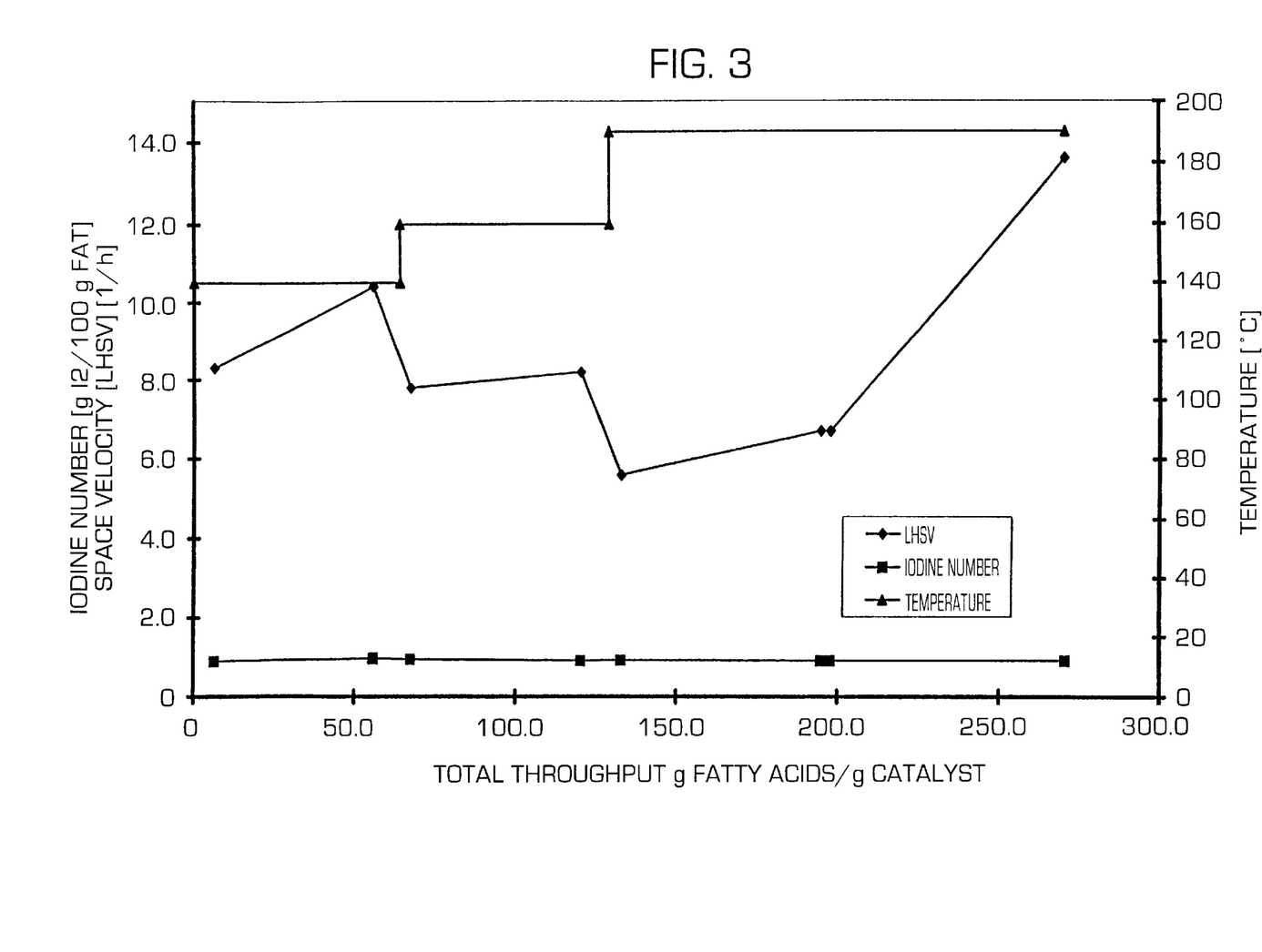
FIG. 3 is a plot of iodine number, temperature and space velocity related to the super critical hardening of fatty acids at 200 bar.

Under the same conditions as in example 1, a life time trial was carried out with crude fatty acid, but without prior extraction. 5 ml of the 1%-Pd/OFP catalyst again came into use. As illustrated in Table 4 and FIG. 3, even at 190° C., only an iodine number of 6 can be attained. A rapid deactivation of the catalyst occurs.

TABLE 4

| Time | T [° C.] | LHSV [h$^{-1}$] | Iodine Number $\frac{g\ I_2}{100\ g}$ | Flow $\frac{g\ Fatty\ Acid}{g\ Catalyst}$ |
|---|---|---|---|---|
| 2.50 | 140.00 | 0.87 | 8.30 | 6.42 |
| 22.53 | 140.00 | 0.95 | 10.40 | 56.04 |
| 26.17 | 160.00 | 0.93 | 7.80 | 67.87 |
| 42.00 | 160.00 | 0.90 | 8.20 | 120.27 |
| 46.25 | 190.00 | 0.91 | 5.60 | 132.85 |
| 66.03 | 190.00 | 0.90 | 6.70 | 194.74 |
| 67.03 | 190.00 | 0.89 | 6.70 | 197.75 |
| 93.25 | 190.00 | 0.89 | 13.60 | 270.65 |

COMPARISON EXAMPLE 2

At 200 bar a comparable hydrogenation was conducted with pure hydrogen in the trickle bed phase, that is without addition of a condensed fluid and without prior extraction. 5 ml of the 1%-Pd/OFP catalyst were used at a hydrogen volume flow of 140 N1/h.

Figure 4:
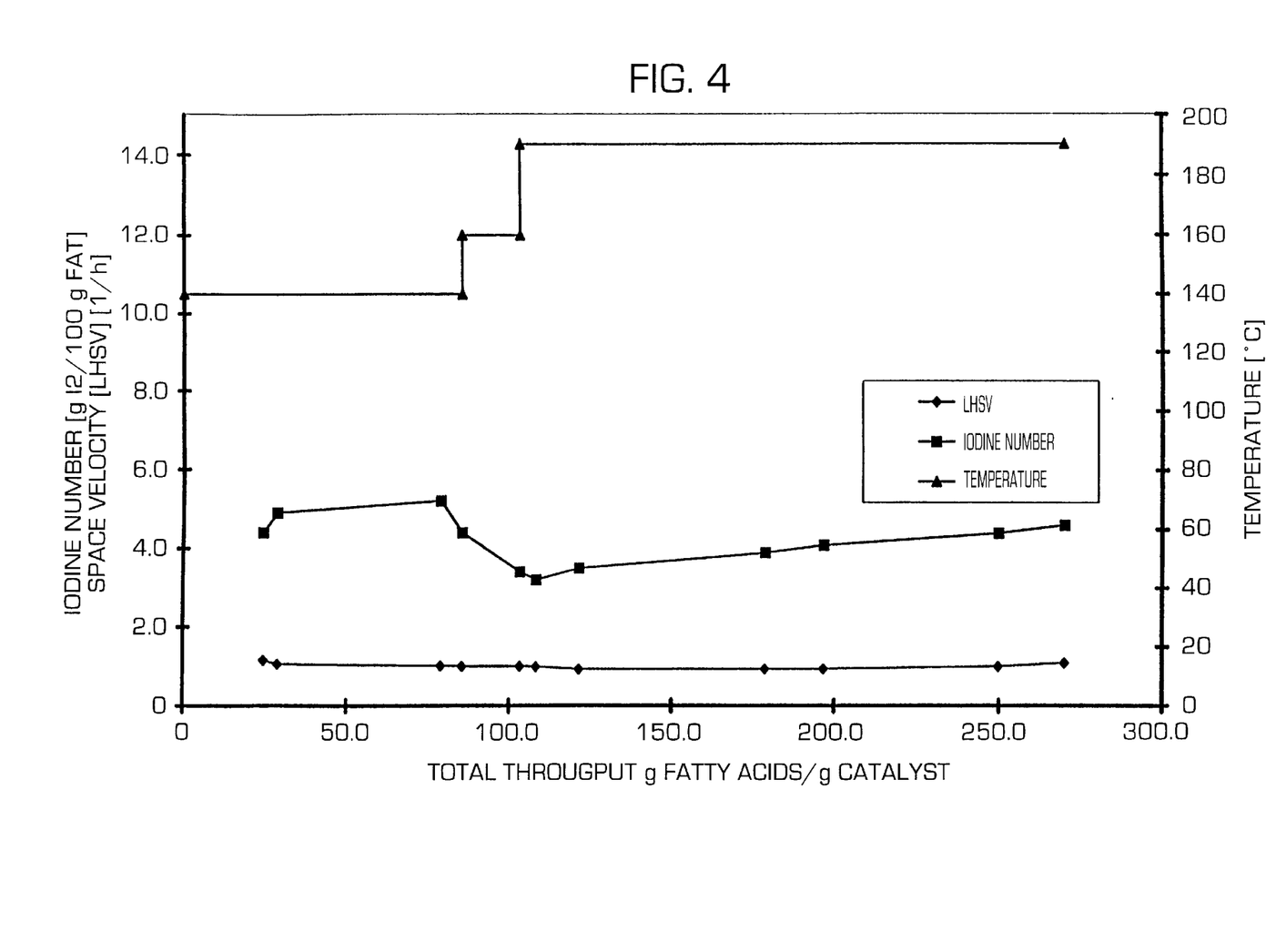
FIG. 4 is a plot of iodine number, temperature and space velocity related to trickle bed hardening of fatty acids at 200 bar.

Table 5 and FIG. 4 describe the hydrogenation process. In comparison to Example 1, higher iodine numbers and a rapid deactivation of the catalyst are observed.

TABLE 5

| Time [h] | T [° C.] | LHSV [h⁻¹] | Iodine Number $\frac{g\ I_2}{100\ g}$ | Flow $\frac{g\ Fatty\ Acid}{g\ Catalyst}$ |
|---|---|---|---|---|
| 6.50 | 140 | 1.15 | 4.4 | 24.1 |
| 7.58 | 140 | 1.05 | 4.9 | 28.3 |
| 24.00 | 140 | 1.01 | 5.2 | 79.2 |
| 26.00 | 160 | 1.00 | 4.4 | 85.6 |
| 32.00 | 190 | 1.00 | 3.4 | 103.3 |
| 33.83 | 190 | 0.98 | 3.2 | 108.4 |
| 38.42 | 190 | 0.92 | 3.5 | 121.8 |
| 54.75 | 190 | 0.93 | 3.9 | 178.6 |
| 61.00 | 190 | 0.93 | 4.1 | 196.7 |
| 78.55 | 190 | 0.99 | 4.4 | 249.8 |
| 85.75 | 190 | 1.08 | 4.6 | 270.2 |

COMPARISON EXAMPLE 3

Figure 5:
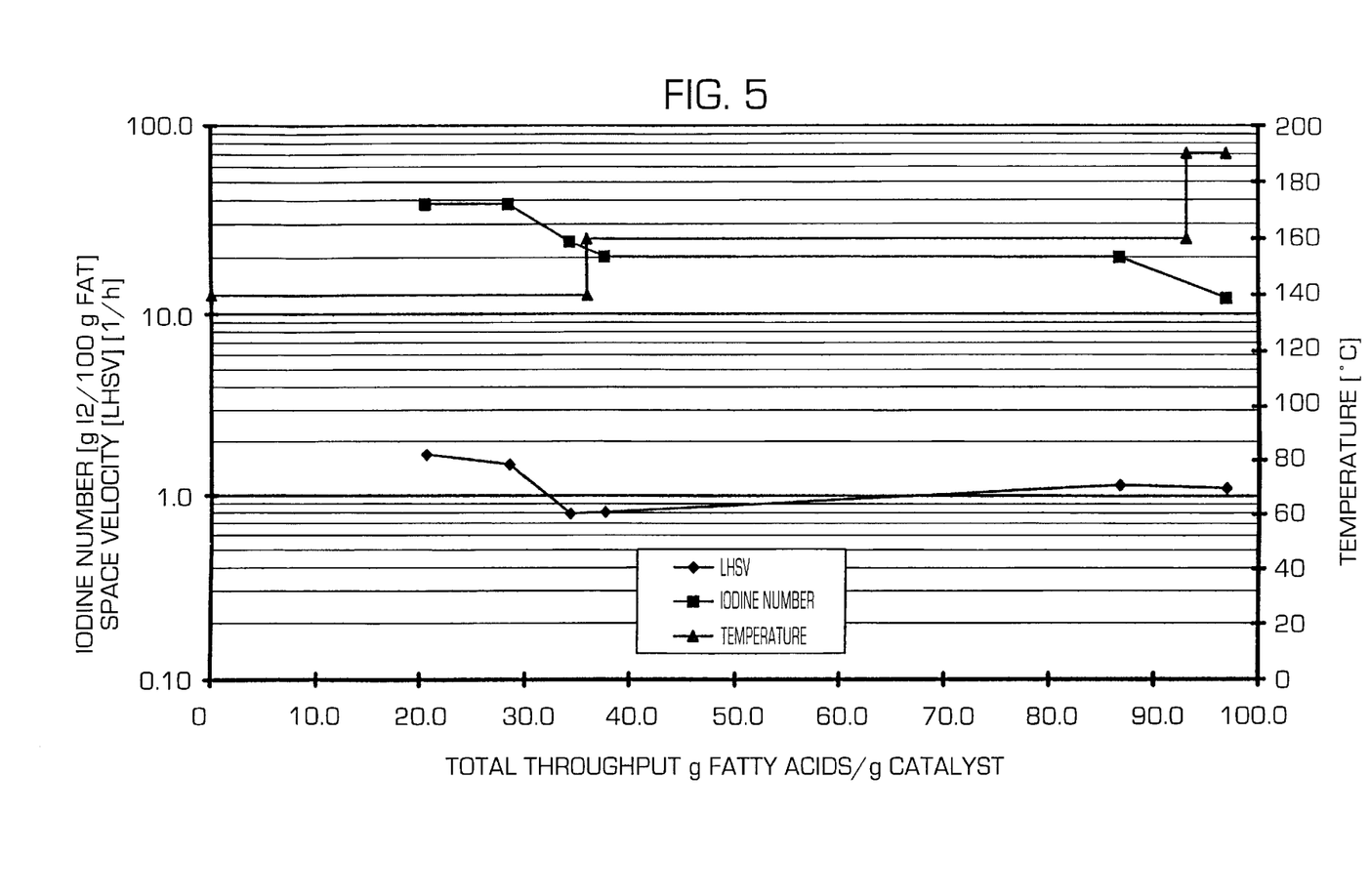
FIG. 5 is a logarithmic plot of iodine number, temperature and space velocity related to trickle bed hardening of fatty acids at 25 bar.

Comparison trial 2 was repeated at a hydrogen pressure of only 25 bar. Table 6 and FIG. 5 describe the course of the hydrogenation. At no point in time of the trial did the iodine number after hardening succeed in lowering to a value under 10.

TABLE 6

| Time [h] | T [° C.] | LHSV [h⁻¹] | Iodine Number $\frac{g\ I_2}{100\ g}$ | Flow $\frac{g\ Fatty\ Acid}{g\ Catalyst}$ |
|---|---|---|---|---|
| 3.67 | 140 | 1.69 | 38.3 | 20.67 |
| 5.25 | 140 | 1.49 | 38.2 | 28.48 |
| 9.33 | 140 | 0.79 | 24.3 | 34.33 |
| 10.58 | 160 | 0.81 | 20.3 | 37.71 |
| 25.58 | 160 | 1.15 | 20.1 | 86.74 |
| 28.50 | 190 | 1.10 | 12.1 | 96.92 |

EXAMPLE 2

Pure linoleic acid ethyl ester is used as the starting substance for a further hydrogenation. An extraction preceding the hydrogenation could thereby be obviated. The hydrogenation was carried out in condensed subcritical propane at a total pressure of 35 bar, a space velocity of 60 h⁻¹ and a reaction temperature of 60° C. 2 ml of the 1%-Pd/OFP catalyst were used.

COMPARISON EXAMPLE 4

Example 2 was repeated with a total pressure increased to 100 bar. Under these conditions, the propane used as fluid is found in a near critical state.

COMPARISON EXAMPLE 5 comparison example 4 was repeated with carbon dioxide instead of propane. At a total pressure of 100 bar and a temperature of 60° C., carbon dioxide is found in a supercritical state.

COMPARISON EXAMPLE 6

The linoleic acid ethyl ester was hydrogenated in a conventional trickle bed hardening, that is without addition of a fluid in pure hydrogen at a pressure of 100 bar.

The results of example 2 and the comparison examples 4 through 6 are listed in Table 7. The measured hydrogenation activity was detected as described in DE 44 05 029.

TABLE 7

Hydrogenation results

| Example | Total pressure [bar] | Fluid | Hydrogen Activity mol $H_2$ hxg act. metal | Remarks |
|---|---|---|---|---|
| B2 | 35 | Propane | 67.2 | subcritical hydrogenation |
| VB4 | 100 | Propane | 104.3 | near critical hydrogenation |
| VB5 | 100 | $CO_2$ | 71.3 | supercritical hydrogenation |
| VB6 | 100 | — | 68.8 | trickle bed hydrogenation |

B2: Example 2; VB4, 5, 6: comparison examples 4, 5, 6

Example 2 and the comparison examples 4 through 6 clearly show that fat raw material, such as fats, oils, fatty acid esters and free fatty acids can be outstandingly hydrogenated with condensed, that is, liquefied, fluids in the subcritical state. The condensed fluids are used in this way as solvent for the fat raw materials. Suitable for this are, for example, the fluids carbon dioxide, propane, ethane, butane, dinitrogen monoxide or mixtures thereof.

As Table 7 shows, in the dissolution of the ethyl ester of linoleic acid ethyl in condensed subcritical propane, comparable hydrogenation activities as in the conventional trickle bed hardening or with the super critical hydrogenation are achieved as per WO 95/22591, however, at a considerably reduced pressure.

The solubility of the employed raw material in the solvent can also here be increased by the use of modifiers. The reaction product is separated after the hydrogenation through pressure release, or temperature increase, of condensed subcritical fluid. The fluid is brought back into the process again, if necessary, after compression, or temperature decrease. The hydrogenation catalysts known in the art come into use.

Further variations and modifications of the invention will be apparent to those skilled in the art from the foregoing and are intended to be encompassed by the claims appended hereto.

German priority application 197 19 431.1 is relied on and incorporated herein by reference.

We claim:
1. A process for the continuous extraction and catalytic conversion of an organic compound which is intermixed with unwanted attendant materials to form a starting substance, the process comprising:
   extracting the desired organic compound from the starting substance by dissolving the organic compound in a condensed fluid in an extraction column in which the starting substance is in countercurrent flow with the condensed fluid, to obtain an extract comprising the condensed fluid and the organic compound, and a waste portion comprising the unwanted attendant materials;
   optionally adding a further reactant and fluid to the extract comprising the condensed fluid and the organic compound;
   contacting the extract with a catalyst for the catalytic conversion of the organic compound, to form a reaction mixture containing a product mixture comprised of individual products of the catalytic conversion;

separating the product mixture from the reaction mixture; and, optionally, returning the fluid which was condensed for further extracting.

2. The process according to claim 1, wherein said extracting and catalytic conversion are carried out at temperatures ranging from 0 to 300° C., and pressures ranging from 10 to 800 bar.

3. The process according to claim 2, wherein the condensed fluid is selected from the group consisting of butane, ethane, carbon dioxide, propane, dinitrogen monoxide and mixtures thereof.

4. The process according to claim 2, further comprising collecting the undesirable attendant materials.

5. The process according to claim 3, wherein the solubility of the organic compound in the condensed fluid is increased through the addition of a modifier to the condensed fluid.

6. The process according to claim 5, wherein the modifier is acetone, a $C_1$–$C_6$ alcohol, or any mixtures thereof.

7. The process according to claim 1, wherein the separating of the product mixture from the fluids is by a lowering of pressure.

8. The process according to claim 7, wherein the separating of the product mixture from the reaction mixture comprises separating the individual products through fractionated pressure reduction or temperature increase.

9. A process for the continuous extraction and catalytic conversion of an organic compound which is intermixed with unwanted attendant materials to form a starting substance, the process comprising:

extracting the desired organic compound from the starting substance by dissolving the organic compound in a condensed fluid to obtain an extract comprising the condensed fluid and the organic compound, and a waste portion comprising the unwanted attendant materials;

optionally adding a further reactant and fluid to the extract comprising the condensed fluid and the organic compound;

contacting the extract with a catalyst for the catalytic conversion of the organic compound, to form a reaction mixture containing a product mixture comprised of individual products of the catalytic conversion;

separating the product mixture from the reaction mixture; and, optionally, returning the fluid which was condensed for further extracting, wherein the organic compound is at least one member selected from the group consisting of a fat, an oil, a fatty acid ester and a free fatty acid, and the catalytic conversion comprises a hydrogenation via hydrogen added as a further reactant.

10. The process according to claim 9, wherein the catalyst is a platinum group metal, nickel or copper, optimally with a promoter, on a formed carrier in a fixed bed.

11. A process for the extraction and the selective or complete hydrogenation of a fatty raw material being at least one member selected from the group consisting of a fat, an oil, a fatty acid and a free fatty acid, the fatty raw material being intermixed with unwanted attendant materials to form a starting substance, the process comprising:

extracting the fatty raw material from the starting substance by dissolving said fatty raw material in a liquefied gas or liquefied gas mixture, to form an extract comprising the fatty raw material, and a waste portion comprising the unwanted attendant materials; and hydrogenating the fatty raw material of the extract in the presence of a hydrogenation catalyst therefor with hydrogen gas at a temperature below the critical temperature for the liquefied gas or the liquefied gas mixture, and at a pressure from 10 to 800 bar.

12. The process according to claim 1, wherein the catalyst for the catalytic conversion of the organic compound is a fixed bed catalyst.

13. The process according to claim 1, wherein the extraction column is electrically heated.

14. The process according to claim 1, wherein the extraction column is electrically heated to obtain a temperature gradient.

15. The process according to claim 14, wherein an extractor head portion of the extraction column is heated to a temperature higher than a remaining portion of the extraction column.

16. The process according to claim 15, wherein the heating of the extractor head portion of the extraction column effects an internal extract reverse movement in the column.

* * * * *